United States Patent

Lingelbach et al.

Patent Number: 5,770,747
Date of Patent: Jun. 23, 1998

[54] PREPARATION OF 1,2-BUTYLENE OXIDE

[75] Inventors: Peter Lingelbach, Mutterstadt; Joachim Roser, Mannheim; Christoph Sigwart, Schriesheim; Werner Schnurr, Herxheim; Hans-Jürgen Weyer, Bobenheim-Roxheim, all of Germany

[73] Assignee: BASF Aktiengesellschaft, Ludwigshafen, Germany

[21] Appl. No.: 765,618

[22] PCT Filed: Jun. 16, 1995

[86] PCT No.: PCT/EP95/02337

§ 371 Date: Dec. 27, 1996

§ 102(e) Date: Dec. 27, 1996

[87] PCT Pub. No.: WO96/00222

PCT Pub. Date: Jan. 4, 1996

[30] Foreign Application Priority Data

Jun. 27, 1994 [DE] Germany .......................... 44 22 046.4

[51] Int. Cl.$^6$ ................................................ C07D 301/00
[52] U.S. Cl. ............................................................ 549/540
[58] Field of Search ............................ 208/144; 549/513, 549/540; 585/275

[56] References Cited

U.S. PATENT DOCUMENTS

| | | | |
|---|---|---|---|
| 2,561,984 | 4/1951 | Hillyer et al. | 568/420 |
| 3,005,832 | 10/1961 | Payne et al. | 549/540 |
| 3,336,241 | 8/1967 | Shokal | 525/507 |
| 4,127,594 | 11/1978 | Anderson et al. | 549/542 |
| 4,897,498 | 1/1990 | Monnier et al. | 549/534 |
| 5,077,418 | 12/1991 | Falling | 549/540 |
| 5,117,013 | 5/1992 | Falling | 549/540 |
| 5,391,773 | 2/1995 | Puckette | 549/540 |

OTHER PUBLICATIONS

Balbolov, E. et al, J. Mol. Catal. 1991, 69(1), pp. 95–103, abstract only.
Aizikovich et al., Catalytic Hydrogenation of . . . , J. General Chemistry of the USSR, vol. 19, No. 1, Jan. 1949.
J. Am. Chem. Soc., vol. 832, 1961, 3096–3113, Yarbell et al.

*Primary Examiner*—C. Warren Ivy
*Assistant Examiner*—Garth M. Dahlen
*Attorney, Agent, or Firm*—Keil & Weinkauf

[57] ABSTRACT

A process for the preparation of 1,2-butylene oxide by the catalytic hydrogenation of vinyl oxirane, in which use is made of a palladium catalyst on a support of barium sulfate, zirconium oxide or titanium dioxide or a rhenium-containing supported palladium catalyst.

6 Claims, No Drawings

PREPARATION OF 1,2-BUTYLENE OXIDE

This application is a 371 PCT/EP95/02337, Jun. 16, 1995.

The present invention relates to a process for the preparation of 1,2-butylene oxide by the catalytic hydrogenation of vinyl oxirane The catalytic hydrogenation of vinyl oxirane over catalysts consisting of palladium on aluminum oxide or palladium on activated charcoal is described in U.S. Pat. No. 5,077,418 and U.S. Pat. No. 5,117,013 and also in *Neftekhimiya* 33, 131 (1993). The yields, selectivities and conversions in this process are unsatisfactory.

It was the object of the present invention to provide a process for the preparation of 1,2-butylene oxide, which makes it possible to prepare 1,2-butylene oxide from vinyloxirane with better conversions, yields, and selectivities than in the prior art.

Accordingly, we have found a process for the preparation of 1,2-butylene oxide by the catalytic hydrogenation of vinyl oxirane, wherein use is made of a palladium catalyst on a support of barium sulfate, zirconium dioxide or titanium dioxide or a rhenium-containing supported palladium catalyst.

When carrying out the process of the invention, the vinyl oxirane or solutions of vinyl oxirane are hydrogenated in a solvent which is inert under the reaction conditions in the presence of the catalysts to be used in the invention at temperatures generally of from $-10°$ to $100°$ C., preferably from $-5°$ to $50°$ C. and more preferably from $0°$ to $30°$ C. under a pressure of from 1 to 100 bar, preferably from 1 to 50 bar, in particular from 1 to 30 bar.

The process of the invention can be carried out without the use of solvents or, advantageously, in the presence of a solvent inert under the reaction conditions, for example, in the presence of alcohols, such as methanol, ethanol, propanol, isopropanol, n-butanol, isobutanol or tert-butanol, hydrocarbons, such as petroleum ether, benzene, toluene or xylene, or dipolar-aprotic solvents, such as N-alkyllactams, eg N-methylpyrrolidone or N-octylpyrrolidone, or, in particular, ethers, such as tetrahydrofuran, dioxane, methyl-tert-butyl ether, di-butyl ether, dimethoxy ethane, diethyl ether or diisopropyl ether.

The process of the invention can be carried out either continuously or batchwise, in the gas phase or in the liquid phase. When the process is carried out continuously, tubular reactors or cascades of reactors can be used for example, which can be operated in the upward-flow mode or downward-flow mode.

Advantageously, the catalysts are arranged in these reactors in the form of a fixed bed. When the process is carried out batchwise, the catalyst can be used, eg, in stirred reactors in the form of a suspension or, advantageously, as a fixed bed, eg, when use is made of recycle reactors.

The palladium content of the catalysts which can be used in the invention is generally from 0.1 to 5 wt %, preferably from 0.3 to 3 wt % and more preferably from 0.5 to 2 wt %, calculated as Pd and based on the total weight of the catalyst.

The rhenium-containing supported palladium catalysts which can be used in the invention contain rhenium in a ratio, by weight, in relation to palladium, generally of 1 to 99, preferably 10 to 90, and more preferably 40 to 60.

Apart from the support materials which can be advantageously used for the catalysts containing only palladium as active ingredient ie barium sulfate, zirconium dioxide, or titanium dioxide, other support materials, such as activated charcoal, silicon dioxide, silica gel, or kieselguhr can also be used to advantage.

The preparation of the palladium catalysts or the catalysts containing palladium and rhenium can be effected in conventional manner, for example, by impregnating the support materials with aqueous solutions of water-soluble compounds of palladium or of palladium and rhenium, for example, with the nitrates, sulfates, halides, or carboxylates of palladium and rhenium, drying the impregnated supports, eg, at temperatures of from $50°$ to $200°$ C., preferably from $100°$ to $150°$ C., then effecting calcination at temperatures generally of from $200°$ to $600°$ C., preferably at a temperature of from $300°$ to $500°$ C., and reducing the catalyst thus obtained by treatment with reducing agents, such as hydrazine, hydrogen, or hydrogenous gases, for example, at temperatures of from $100°$ to $300°$ C., preferably at a temperature of from $150°$ to $250°$ C. When carrying out reduction and activation of the catalyst with hydrogen, reduction is generally continued until no more appreciable amounts of water are formed.

The reduction and activation of the catalysts with hydrogen can take place in situ in the hydrogenating reactor during hydrogenation, but the catalysts are preferably reduced and activated prior to their use in the process of the invention.

When use is made of thermally unstable salts of palladium and rhenium for impregnation of the support material the activation of the catalyst can alternatively take place thermally by heating the impregnated supports to temperatures generally of from $100°$ to $700°$ C., and preferably of from $200°$ to $600°$ C.

Instead of using the aforementioned palladium or rhenium salts, water-soluble palladium complex compounds or water-soluble salts of the oxyacids of rhenium, for example, alkali metal or ammonium rhenates or perrhenates and solutions of rhenium heptoxide ($Re_2O_7$) can be used for impregnation of the supports.

When preparing palladium and rhenium-containing supported catalysts, the elements rhenium and palladium can be applied to the support material simultaneously or successively for impregnation of the support material.

The purification of the reaction mixture in order to isolate 1,2-butylene oxide can take place in conventional manner, eg, by distillation.

The vinyl oxirane required as starting material can be prepared, eg, by the method described in U.S. Pat. No. 4,897,498 by partial oxidation of 1,3-butadiene over silver catalysts.

1,2-butylene oxide can be used, eg, as fuel additive or as stabilizer for chlorinated hydrocarbons.

EXAMPLES

Hydrogenation of vinyl oxirane to 1,2-butylene oxide was carried out in a stirred autoclave having a capacity of 50 mL. In each case, the reactor was charged with 0.1 g of the respective catalyst and 2.5 g of vinyl oxirane in 22.5 g of tetrahydrofuran.

The hydrogenating conditions temperature, pressure, and residence time and the degree of hydrogenation obtained (determined by calibrated gas chromatography of the hydrogenated effluent) are listed in the table.

TABLE

| Catalyst* | Hydrogenation Temperature [°C.] | Pressure [bar] | Residence Time [h] | Conversion [%] | Yield [%] | | |
|---|---|---|---|---|---|---|---|
| | | | | | 1,2-B | BA | n-BuOH |
| 0.5% Pd/BaSO$_4$ | 20 | 20 | 9 | 100 | 67 | 14 | 11 |
| 1% Pd/BaSO$_4$ | 0 | 4 | 15 | 100 | 82 | 4 | 6 |
| 1% Pd/BaSO$_4$ | 0 | 20 | 12 | 100 | 81 | 5 | 2 |
| 1.5% Pd/BaSO$_4$ | 20 | 4 | 15 | 100 | 70 | 17 | 10 |
| 1% Pd/ZrO$_2$ | 20 | 8 | 15 | 100 | 60 | 20 | 14 |
| 3% Pd + 3% Re/C | 0 | 20 | 11 | 100 | 75 | 6 | 9 |
| 0.5% Pd + 0.5% Re/Al$_2$O$_3$ | 50 | 40 | 8 | 100 | 71 | 9 | 8 |

*Percentages by weight, based on total catalyst
1,2-B: 1,2-butylene oxide
BA: n-butyraldehyde
n-BuOH: n-butanol

We claim:

1. A process for the preparation of 1,2-butylene oxide by the catalytic hydrogenation of vinyl oxirane, wherein a palladium catalyst on a support of barium sulfate, zirconium dioxide or titanium dioxide or a rhenium-containing supported palladium catalyst is used.

2. A process as defined in claim 1, wherein use is made of a palladium catalyst having a palladium content of from 0.1 to 5 wt %.

3. A process as defined in claim 1, wherein use is made of a palladium catalyst having a palladium content of from 0.3 to 3 wt %.

4. A process as defined in claim 1, wherein the hydrogenation is carried out at a temperature of from −10° to 100° C. and under a pressure of from 1 to 100 bar.

5. A process as defined in claim 1, wherein the hydrogenation is carried out in a solvent.

6. A process as defined in claim 1, wherein the hydrogenation is carried out in a dipolar-aprotic solvent.

* * * * *